(12) United States Patent
Suh et al.

(10) Patent No.: US 7,657,389 B2
(45) Date of Patent: Feb. 2, 2010

(54) METHOD OF ALIGNING PROBE FOR EDDY CURRENT INSPECTION

(75) Inventors: Ui W. Suh, Cincinnati, OH (US); Richard C. Knepfle, Mason, OH (US)

(73) Assignee: General Electric Company, Schenectady, NY (US)

( * ) Notice: Subject to any disclaimer, the term of this patent is extended or adjusted under 35 U.S.C. 154(b) by 406 days.

(21) Appl. No.: 11/466,503

(22) Filed: Aug. 23, 2006

(65) Prior Publication Data

US 2007/0244659 A1    Oct. 18, 2007

Related U.S. Application Data

(60) Provisional application No. 60/744,693, filed on Apr. 12, 2006.

(51) Int. Cl.
*G01D 18/00* (2006.01)
*G06F 19/00* (2006.01)
*G06F 17/40* (2006.01)

(52) U.S. Cl. .................. 702/104; 73/1.01; 324/200; 702/33; 702/35; 702/38; 702/85; 702/127; 702/189

(58) Field of Classification Search .................. 73/1.01, 73/865.8, 866.5; 324/200, 222; 702/1, 33, 702/34, 35, 38, 85, 86, 87, 90, 104, 105, 702/127, 187, 189
See application file for complete search history.

(56) References Cited

U.S. PATENT DOCUMENTS 5,481,916 A * 1/1996 Macecek et al. .............. 73/601
6,907,358 B2   6/2005 Suh et al.

* cited by examiner

*Primary Examiner*—Edward R Cosimano
(74) *Attorney, Agent, or Firm*—McNees Wallace & Nurick, LLC

(57) ABSTRACT

A system and method using a touch probe device for eddy current inspection. The touch probe provides a simple approach for coming within close contact of the specimen while maintaining a normal angle and pressure at the right positions. The use of the touch probe further reduces the total time for the eddy current inspection. The touch probe aligns the probe to a specimen to be inspected, for the purpose of reducing measurement errors and increasing productivity.

25 Claims, 8 Drawing Sheets

METHOD OF ALIGNING PROBE FOR EDDY CURRENT INSPECTION

CROSS REFERENCE TO RELATED APPLICATIONS

This application claims the benefit of expired Provisional Application No. 60/744,693 filed Apr. 12, 2006, the complete disclosure of which is incorporated herein by reference.

FIELD OF THE INVENTION

The present invention is directed to a method of automatic alignment for eddy current inspection using a Touch probe (TP).

BACKGROUND OF THE INVENTION

Eddy current (EC) inspection is commonly used to detect flaws in material properties such as residual stress, density, and degrees of heat treatment, as well as detect any cracks, pings, dings, or raised material on surfaces of manufactured components such as gas turbine engine components. EC inspection is required for most aircraft engine components on which abnormal indications are detected to ensure the engine's integrity until the next maintenance schedule. During this type of inspection, electromagnetic induction is used to induce eddy currents in the component being inspected. An array of coils inside an eddy current probe generates alternating magnetic fields, which induce the eddy currents when the probe is moved near the component. When flaws are present in the component, the flow of eddy currents is altered, thereby indicating the flaw to the inspector. The altered eddy currents produce changes in a secondary magnetic field, which are detected by the array of coils inside the eddy current probe. The array generates an electrical signal in response to the altered secondary magnetic field, where the amplitude of the electrical signal is generally proportionate to the size of the flaw.

In order to effectively inspect the surface and maintain the integrity of the EC signal, smaller sized coils are used to enable maneuvering around the surface of the component. A small coil typically used is around 0.02 inches, and is effective at detecting any imperfections in the surface of the component, however these small coils are also extremely sensitive to the inspection equipment. Further, the coil has to travel with a constant pressure in relation to the specimen. To enable easier inspection of the components with the probes, the probes are often designed smaller, so they can fit into the smaller areas of the component surface. Changes in the probe shape prevent the probe from being positioned a uniform distance from the inspected component. Further, due to variations in size and shape of the component being inspected, gaps sometimes occur between the probe and the component surface, which also prevents the probe from being positioned at a uniform distance from the component. For years it has been a challenge to place a moving probe in close proximity with the component while maintaining a normal angle and normal pressure at positions sufficient for accurate readings. Even with the current, more sophisticated methods and probes available on market, the procedure to align the probe for inspection can be very time consuming, where the small features of the components are particularly difficult to align with the probe.

One current method for EC inspections uses an alignment template for each individual inspection feature. The EC probe is aligned with the alignment template, which results in an accurate inspection, assuming the template is correctly aligned with the component. This alignment template method requires the construction of a precise template, repeating the steps of realigning the template to the component, aligning the probe to template, detaching the template, and finally checking the probe alignment with the component. This current method adds the unnecessary high cost of producing the templates as well as high labor costs and delays timely delivery.

Another method for EC inspection, described in "Eddy current inspection Method" U.S. Pat. No. 6,907,358, improves the alignment process and increases productivity. However, this method is a manual process that is slow and cumbersome. Because the alignment of the EC touch probe for EC inspection is visually or audibly checked manually by a technician to ensure that no gap existed between the probe and the component surface, the component was required to be re-inspected due to the changes in the various technician's perception. Also, this method is dangerous, as to effectively hear or see the probe touching the component surface, the technician often has to dangerously place his or her head near the moving parts, or bend and twist into uncomfortable positions to ensure that the alignment is correct. Further, some areas that require inspection are small and located between engine blades or in unreachable cavities. Since these areas are difficult and often impossible to reach, the manual alignment method cannot effectively inspect those areas. Lastly, since the manual alignment method is time consuming and often consumes a significant amount of a technician's time. Because so much of a technician's time is dominated by the alignment method, the method is costly as well.

Therefore what is needed is a method and system that is directed to an accurate and efficient EC inspection process that can reduce errors, alleviate safety concerns, and lower production costs.

SUMMARY OF THE INVENTION

A method for aligning a probe for eddy current inspection of a component includes characterizing a touch probe with a calibration plate to find a probe radius and a probe offset of the touch probe, aligning a component to be inspected with the touch probe to locate and place a virtual zero point of a model of the component to a virtual zero point of the component and transferring a virtual zero point of the touch probe to a virtual zero point of the eddy current probe. The probe radius and the probe offset are entered into coordinates that are transferred to the eddy current probe to compensate for a plurality of offsets between the touch probe and the eddy current probe during the step of aligning the component with the touch probe.

A method for eddy current inspection of a component includes aligning an eddy current probe for eddy current inspection of the component using a touch probe, initializing a scan plan of the component and completing the eddy current inspection of the component. The touch probe is used with the scan plan to reduce time and errors associated with eddy current inspection.

One advantage of the present invention is the elimination of the alignment template, which results in a more efficient and cost effective inspection.

Another advantage of the present invention is reduced errors and increased accuracy because the amount of user set-up is reduced.

Yet another advantage of the present invention is that the touch probe itself is the alignment tool and does not require any parameter adjustments. The elimination of the parameter adjustment reduces the inspection time greatly compared to past methods, in which adjustments were repeated several times to gain the desired accuracy for the inspection.

Another advantage of the present invention is the use of an industrial type touch probe, which produces accurate repeatability with inspections, to reduce errors and time consumption.

An additional advantage of the present invention is that the positioning accuracy at the component surface is improved, thereby reducing errors.

Another advantage of the present invention is the pressure between the probe and component is consistent, thereby producing a clean and precise EC signal for the inspection.

Another advantage of the present invention is the reduction of human errors and an increase of safety because the probe performs the alignment automatically.

Other features and advantages of the present invention will be apparent from the following more detailed description of the preferred embodiment, taken in conjunction with the accompanying drawings which illustrate, by way of example, the principles of the invention.

BRIEF DESCRIPTION OF THE DRAWINGS

Wherever possible, the same reference numbers will be used throughout the drawings to refer to the same or like parts.

DETAILED DESCRIPTION OF THE INVENTION

Figure 1:
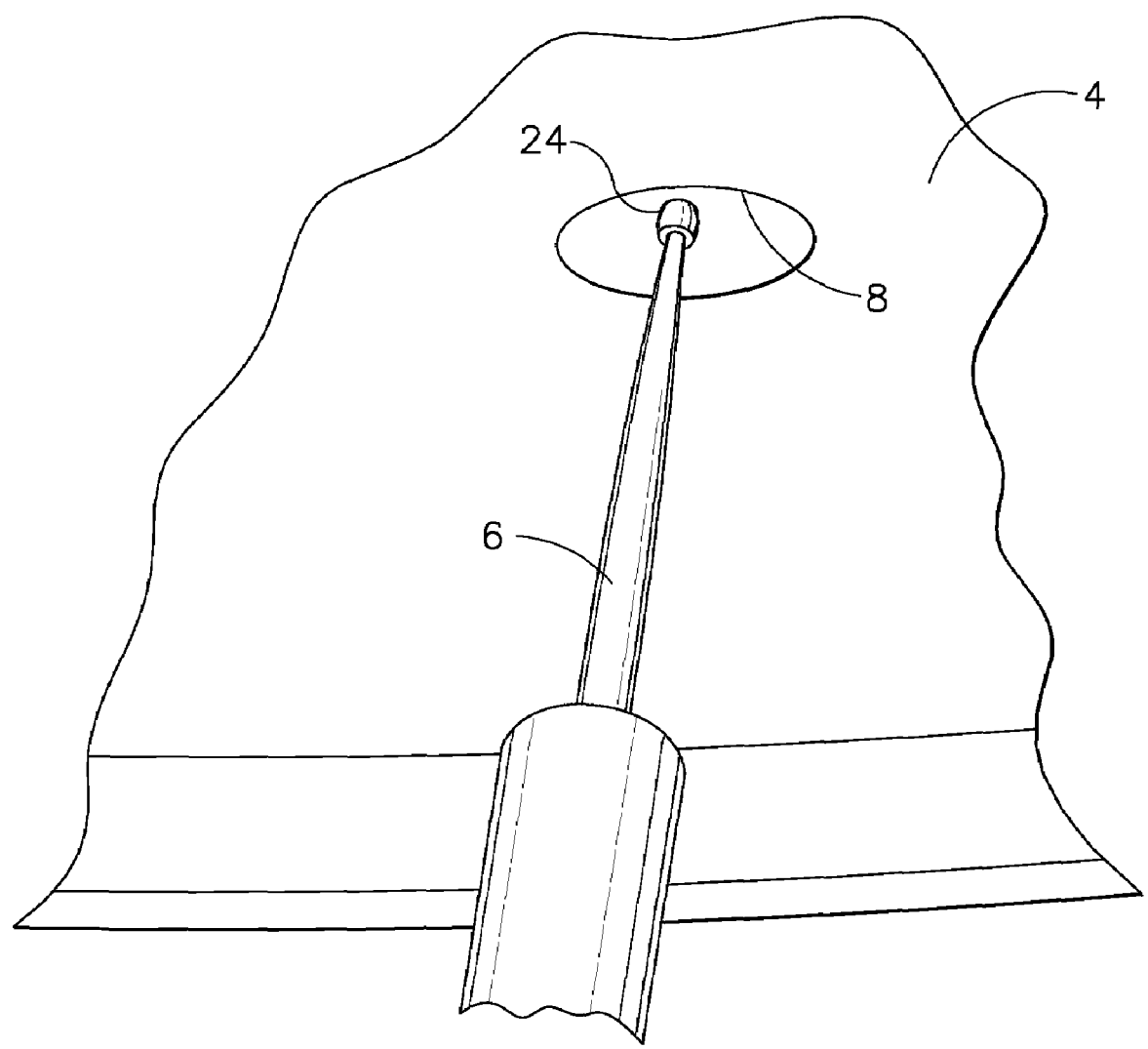
FIG. 1 is an illustration of the of the eddy current probe performing an eddy current inspection of a component.
Figure 2:
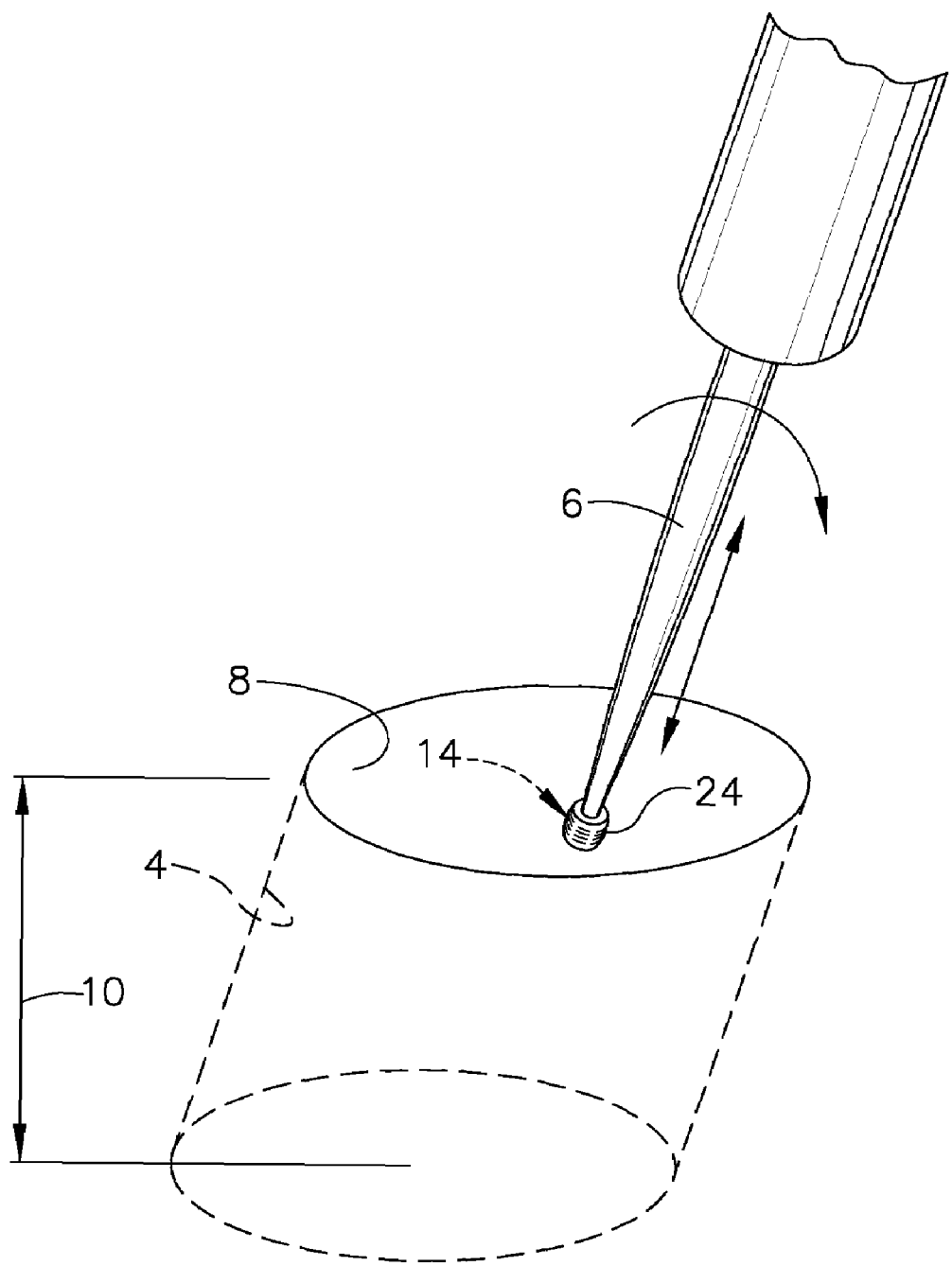
FIG. 2 is a schematic of eddy current inspection of the inside of a component using an EC probe.

A touch probe is used to align the EC probe for eddy current inspection of manufactured components such as gas turbine engine components. FIG. 1 illustrates the eddy current inspection of an oil drain hole 8 of a component. While FIG. 1 is shown and described as the feature being inspected, any feature or surface requiring inspection may be utilized. The eddy current probe 6 is placed inside the oil drain hole 8 as shown in FIG. 2, or near the component for inspection. An alternating current through the probe coil 14 (not shown) produces eddy currents in the component surface 4. The reaction of the eddy currents in the component surface 4 are monitored by the probe 6 and are sent to a computer to process. Before the inspection can be initiated, however, several steps must be performed by using a touch probe to correctly align the eddy current probe 6 to ensure accurate results. Lift-off, the gap between the EC probe 6 and the component surface 4, must be eliminated during inspection. Even a lift-off as small as 0.001 inch could affect the results of the inspection, therefore, there must be direct contact between the probe 6 and the component surface 4 during the entire inspection process. The alignment of the probe 6 with the component surface eliminates the lift-off effect during inspection, and helps to maintain consistent probe pressure on the component 10 during the inspection process, which produces accurate results.

Figure 5:
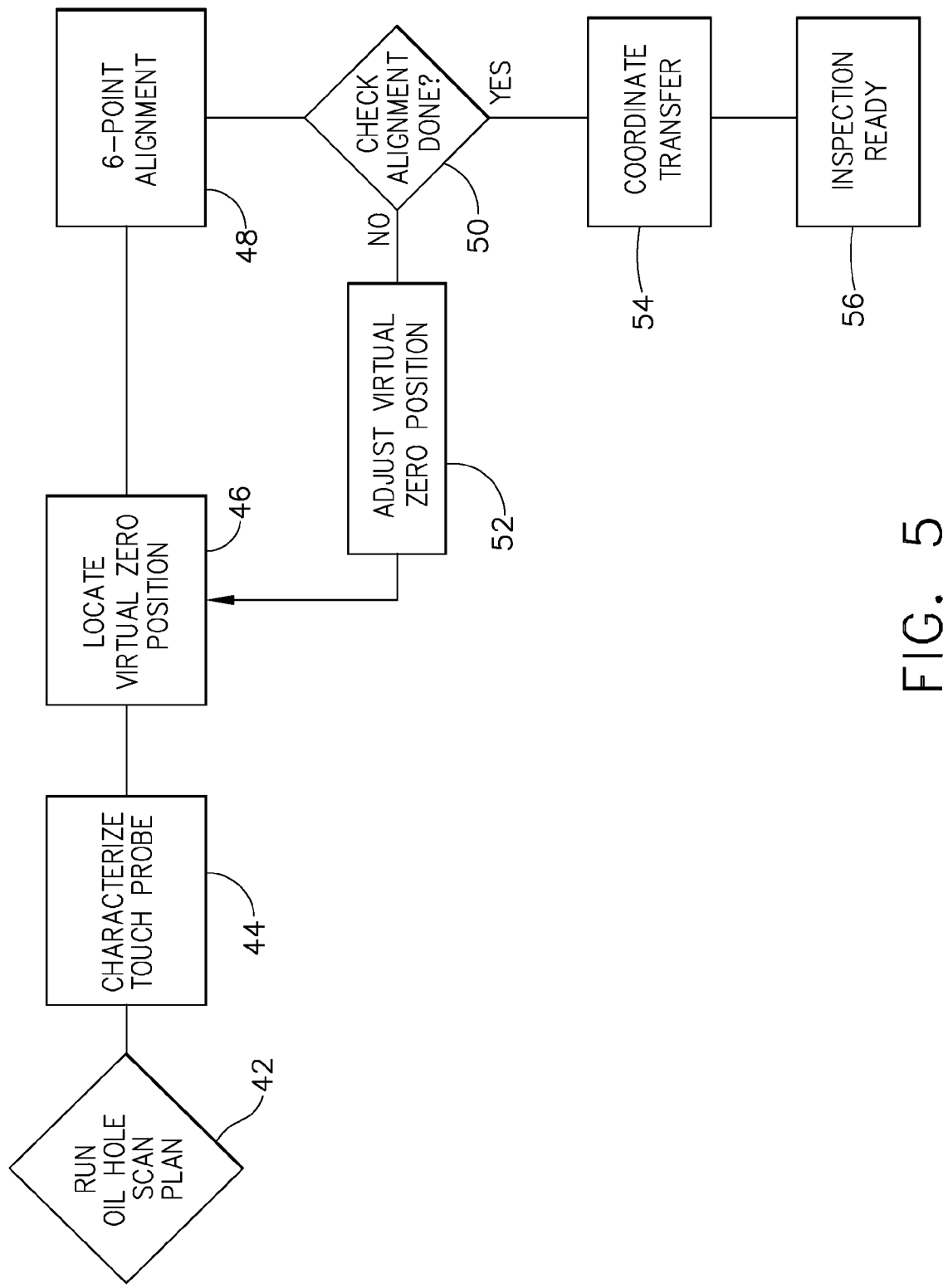
FIG. 5 is a flow chart of the alignment of the touch probe with the component.

There are three steps to accomplish the EC probe alignment with the component 10 as described in FIG. 5. In summary, the three steps include a touch probe 12 (not shown) used to reduce any errors once the EC probe 6 (not shown) is used. First, the touch probe 12 is characterized with the calibration plate 26 to find the probe radius 18 and the probe offset 20. The radius 18 and offset 20 of the probe are necessary to compensate for any physical bending or imperfection in the probe during the alignment and inspection. The probe radius 18 and offset 20 values are inserted into coordinates and eventually transferred to the EC probe 6 to compensate for any imperfections during the inspection process. These compensations further eliminate lift-off effect during inspection.

Figure 3A:
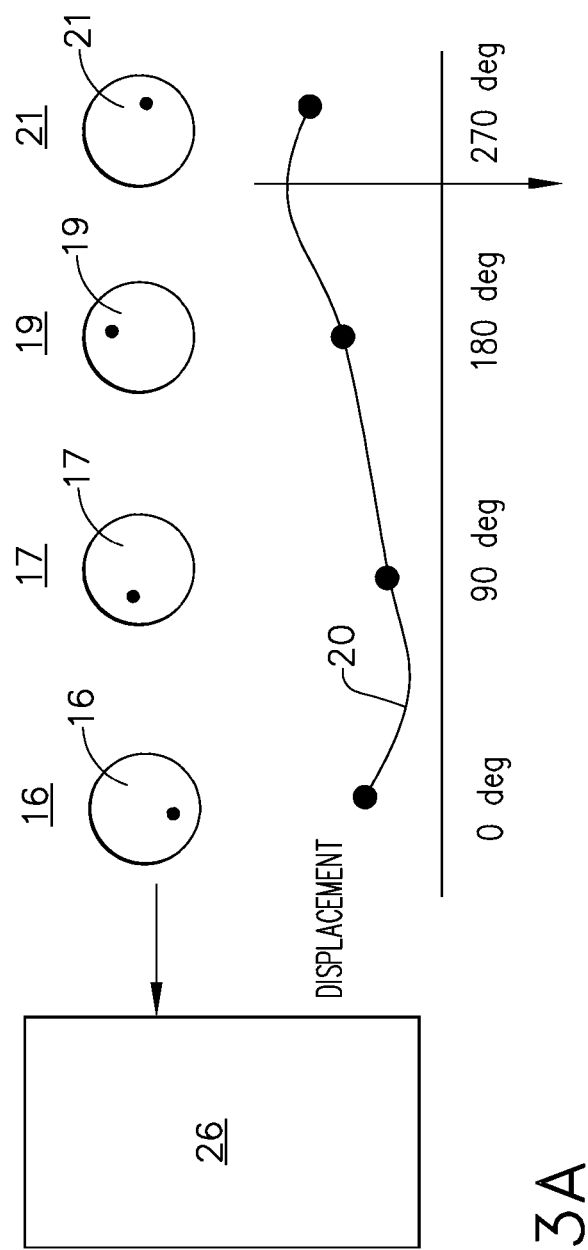
FIG. 3A is an illustration of the characterization of a touch probe.

The first step is shown schematically in FIG. 3A, where the touch probe 12 is configured to find the probe radius 18, the probe offset 20 relative to the center of rotation of the component 10 and the angle 22 of the touch point with the component 10. This step requires additional alignment when the component 10 contains features such as dovetails, oil drain holes, or Lock&Load slots, a generic term or abbreviation for locking slot and loading slot. Referring back to FIG. 2, when the component 10 contains features such as dovetails, oil drain holes, or Lock&Load slots, the EC probe 6 must be aligned for those features to ensure accurate inspection of the component 10. The EC probe 6 follows an exact scan path, or the exact feature shape. This exact path or feature shape is obtained from the part drawings. A UniGraphics (UG) model of the component 10 is composed based on the part drawings before the actual inspection begins so the EC probe coil 14 can be placed in the desired position of the component 10 without having to calibrate the coil 14 numerous times before the probe 12 is in the desired location. A UG model is used for ease of data extraction and easier viewing of the part, and further eliminates the time consuming alignment procedures previously used for EC Inspection. Before the EC probe 6 is placed for inspection, the inspection path is obtained from the UG model by overlaying the model on the component 10. The probe 6 is aligned to the UG model of the component 10, which is an overlay of the component 10, thus during inspection, the probe 6 follows the same path that was determined during inspection with the overlay.

Figure 3B:
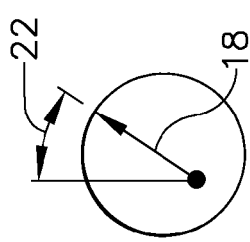
FIG. 3B is an illustration of the probe radius and probe alignment.

As part of the touch probe configuration, the touch probe 12 is configured to interrupt the computer process when the stylus 24 contacts the calibration plate 26. Contact occurs during the first step, when the probe 12 is obtaining axis positions. As shown in FIG. 3A, the axis is found by rotating the touch probe 12 to zero degrees 16 and moving the touch probe 12 towards the calibration (CAL) plate 26. The next axis position is found at ninety degrees 17, then at one hundred and eighty degrees 19, and lastly at two hundred and seventy degrees 21. The existing flat surface of the CAL plate 26 is used for measuring the radius and angle of the TP stylus 24. The information of the TP radius and angle is needed to rotate the same TP stylus 24 to each alignment touch point of the component. When the probe 12 touches the calibration plate 26, the displacement axis position 20 is recorded. As shown in FIG. 3B, the probe radius 18 (TP_Radius) and the probe's angle of alignment 22 (TP_TiltAngle) is computed by using the following equations:

$$TP\_Radius = ((Posit\_0\text{-}Posit\_180)*(Posit\_0\text{-}Posit\_180) + (Posit\_90\text{-}Posit\_270)*(Posit\_90\text{-}Posit\_270))/2 + TP\_dia/2 \quad \text{Equation 1}$$

$$TP\_TiltAngle = RadToDeg*ATAN(Posit\_90\text{-}Posit\_270)/(Posit\_0\text{-}Posit\_180)) \quad \text{Equation 2}$$

Figure 6:
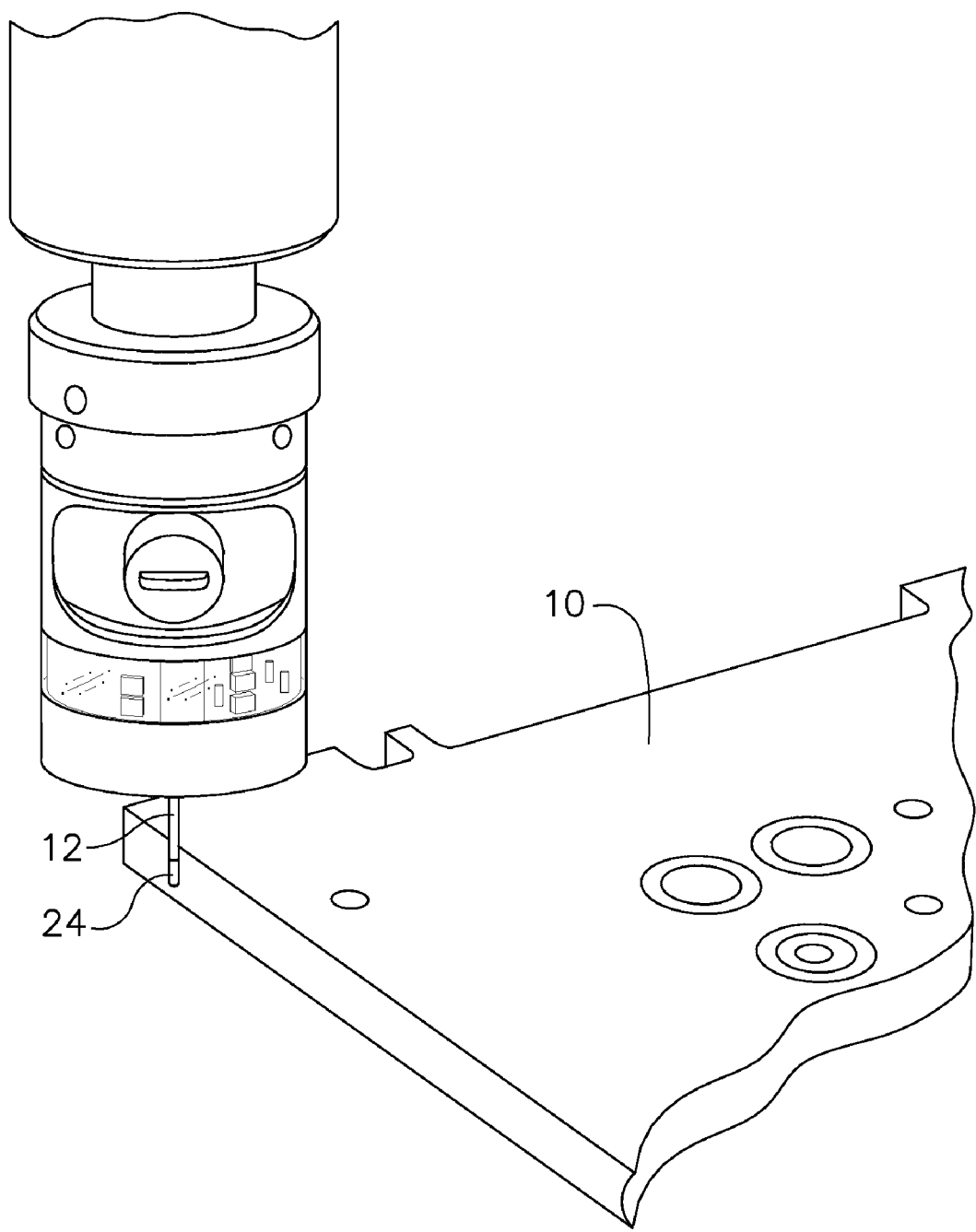
FIG. 6 is an illustration of the characterization of the touch probe with the component.

The characterization of the touch probe 12 is shown in FIG. 6, where the probe 12 is calibrating the radius 18 and the angle 22 for accurate EC inspection of the component 10.

Figure 4B:
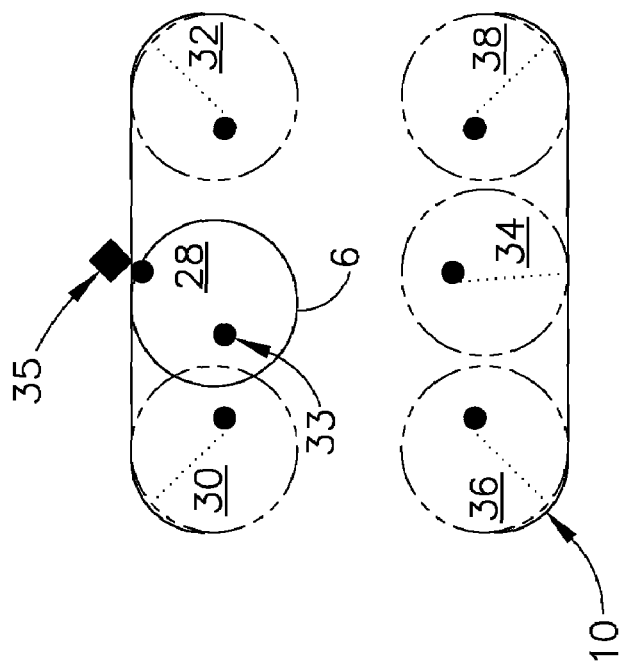
FIG. 4B is a schematic of the alignment of the eddy current probe for the coordinate transfer from the touch probe to the eddy current probe.
Figure 4A:
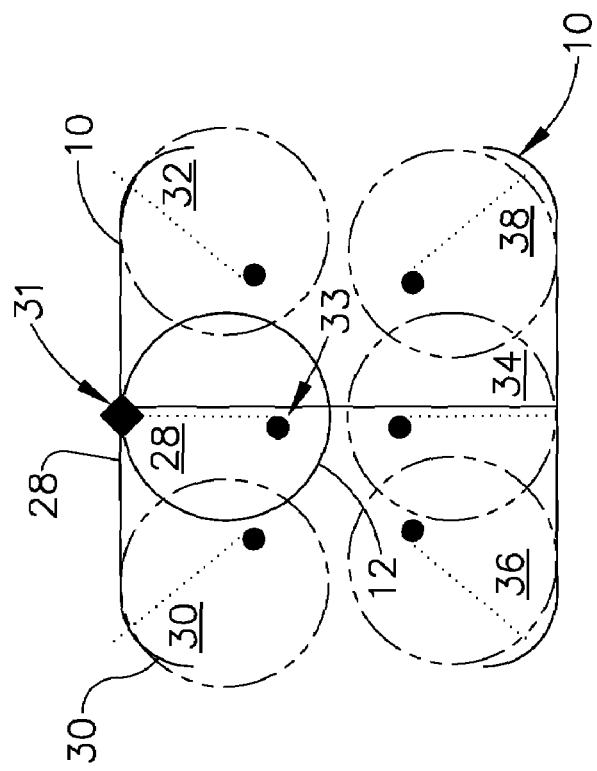
FIG. 4A is a schematic of the alignment of the touch probe for the coordinate transfer from the touch probe to the eddy current probe.
Figure 7:
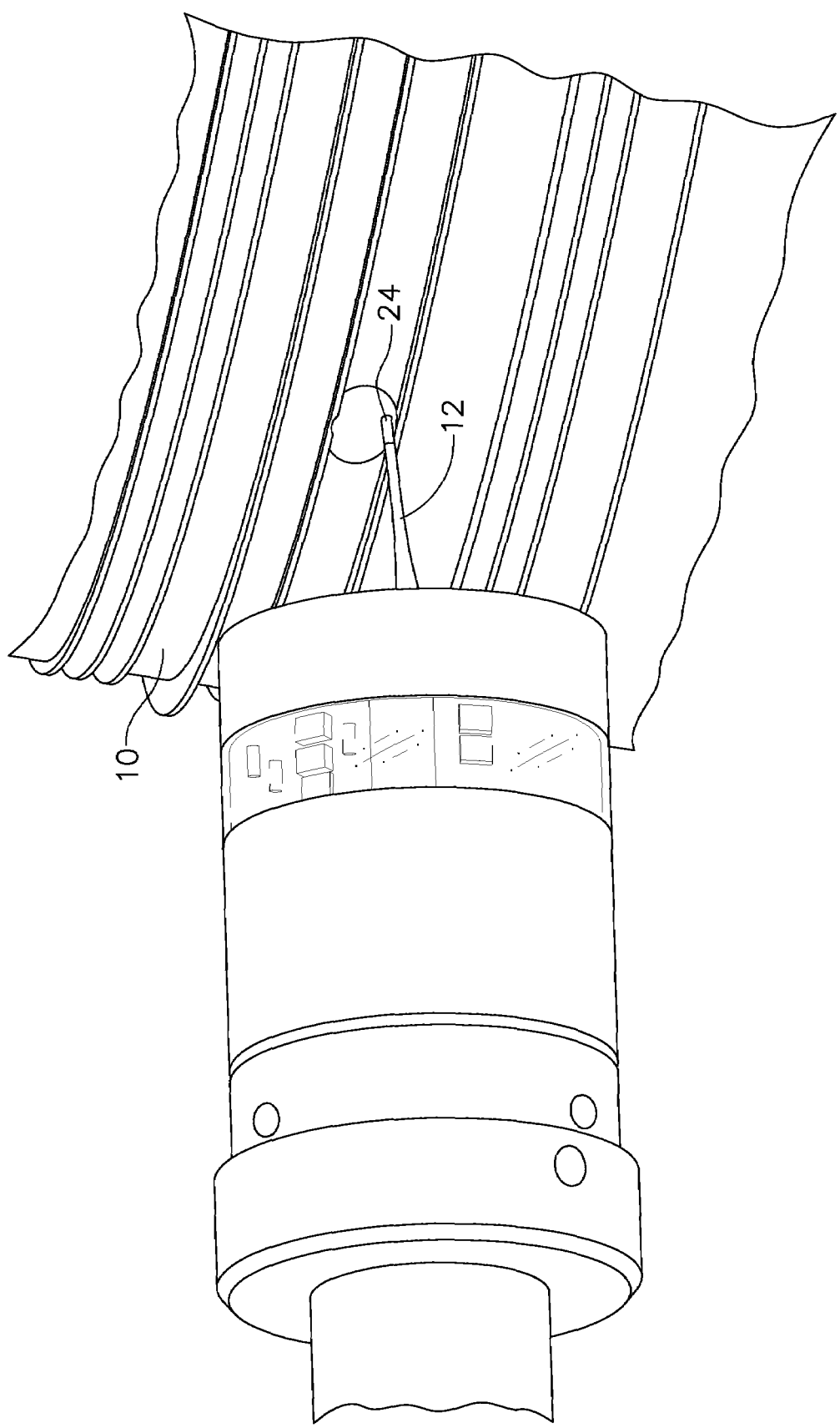
FIG. 7 is an illustration of the auto-alignment of the touch probe and the component.

As shown in FIG. 7, the second step of the alignment is to align the component 10 with the touch probe 12 in order to locate and place the UG model's virtual zero point with the component's virtual zero point automatically. As shown in FIG. 4A, to find the virtual zero point 31 of the touch probe 12 (not shown), the touch probe 12 touches the component 10 sequentially beginning at the top-center 28, then moving to the top-left 30 of the component 10, then to the top-right 32, moving to the bottom 34, bottom-left 36, and lastly, the bottom-right 38 of the component 10. By having contact with the left and right, or top and bottom of the component 10, a true center of the component 10 is calibrated depending upon where the center of rotation 33 is located at each touch point 28, 30, 32, 34, 36, 38. FIG. 4B illustrates how the EC probe 6 then follows the same path the touch probe completed in FIG. 4A, touching the top-center 28, then moving to the top-left 30 of the component 10, then to the top-right 32, moving to the bottom 34, bottom-left 36, and lastly, the bottom-right 38 of the component 10. The virtual zero point 33 of the touch probe is transferred to the EC probe 6 and becomes the virtual zero point 35 of the EC probe 6. One embodiment of the invention requires approximately three minutes to align the touch probe 12 to the component 10, and may be repeated more than 3 times if a higher accuracy is required or desired. The alignment process is shown in FIG. 7, where the probe is aligned for the component's virtual zero point with the UG model's virtual zero point.

The third step in the alignment process of the probe 12 and the component 10 before actual inspection of the component 10 is to transfer the virtual zero 31 aligned with the touch probe 12 to virtual zero 35 of EC probe 6 as shown in FIGS. 4 and 4A. The EC probe's virtual zero point 35 is adjusted by the offset values calculated from the following equations:

$$REL\_X\_ZERO = -1*(TP\_Radius)*Cos\ U \quad \text{Equation 3}$$

$$REL\_Y\_ZERO = (ProbeOffset/2) \quad \text{Equation 4}$$

$$REL\_Z\_ZERO = (TP\_Radius)*Sin\ U, \text{ Where U is angle for vertical rotation axis, to EC Probe virtual zero} \quad \text{Equation 5}$$

Figure 8:
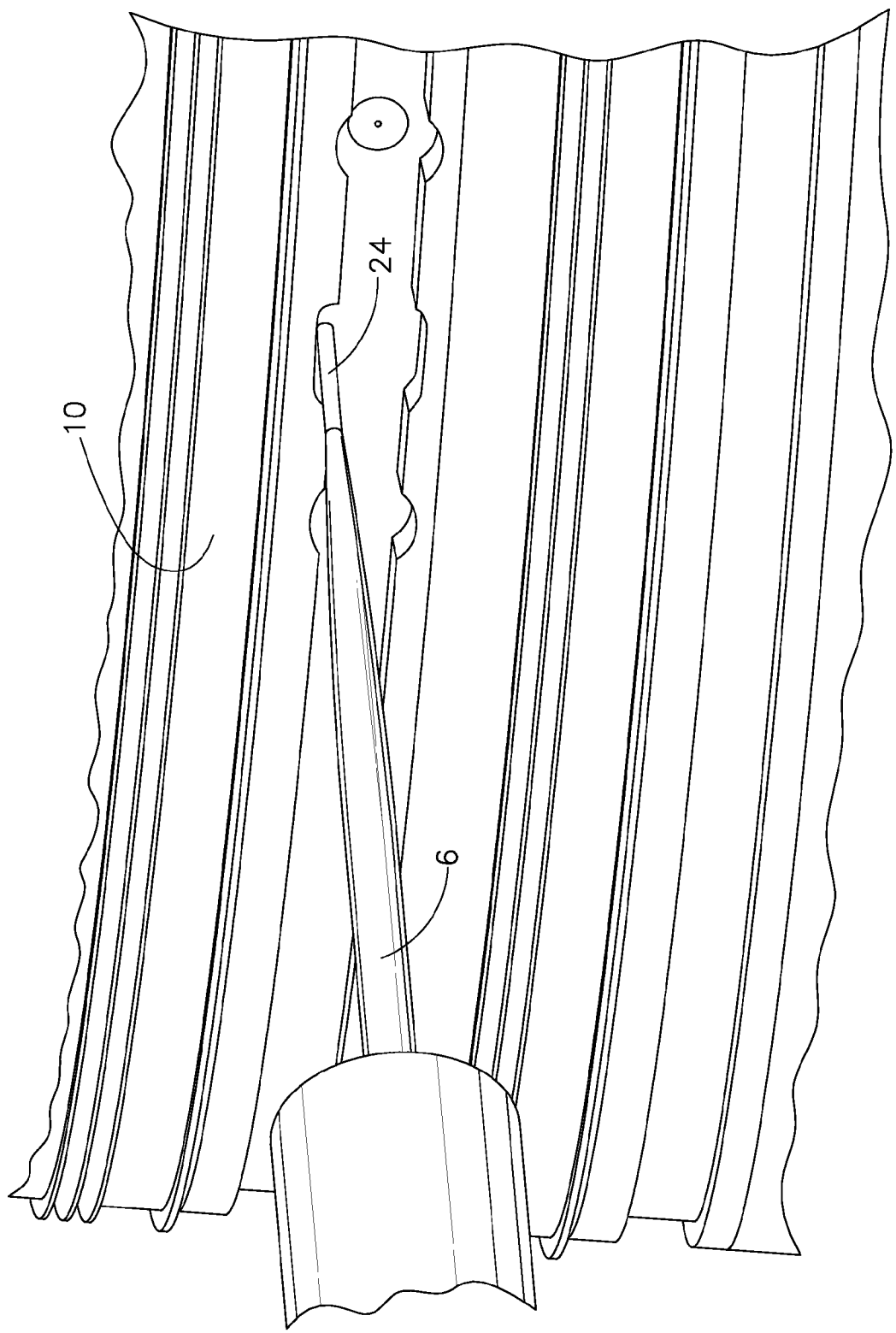
FIG. 8 is an illustration of eddy current inspection of a component with the eddy current probe.

After the coordinates are transferred from the touch probe 12 to the EC probe 6, the EC probe 6 is placed at the UG model virtual zero point (not shown). The EC probe 6 follows scan points derived from UG model, as shown in FIG. 8.

FIG. 5 shows the process of the three steps to initialize the EC inspection process by aligning the touch probe 12 with the component 10. First, in Step 42, an EC scanplan is started for inspection. A scan plan, for example, is when the touch probe 12 is placed inside the oil hole of a gas turbine engine, searching for stresses or areas of weakness that could cause errors or component failures. The touch probe 12 is characterized in Step 44 as described in greater detail above. Step 46 locates the virtual zero 33 position of the touch probe 12 with the component 10, also as described above in greater detail. Step 48 involves configuring the six-point alignment with the component. The alignment is checked for completeness in Step 50. If the alignment is complete, then the coordinates are transferred in Step 54 to the eddy current probe 6 from the touch probe 12. Then in Step 56 the inspection is ready and can be initiated, as illustrated in FIG. 8. If the alignment is not complete in Step 50, then the virtual zero 33 position is adjusted in Step 52. Then step 46 is repeated to find the actual virtual zero 33 position, and Step 48 is also repeated to check the alignment once again.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for aligning a probe for eddy current inspection of a component comprising:
   characterizing a touch probe with a calibration plate to find a probe radius and a probe offset of the touch probe;
   aligning a component to be inspected with the touch probe to locate and place a virtual zero point of a model of the component to a virtual zero point of the component;
   transferring a virtual zero point of the touch probe to a virtual zero point of the eddy current probe; and
   wherein the probe radius and the probe offset are entered into coordinates that are transferred to the eddy current probe to compensate for a plurality of offsets between the touch probe and the eddy current probe during the step of aligning the component with the touch probe.

2. The method of claim 1 wherein the step of characterizing a touch probe further comprises computing the touch probe offset based on the probe radius.

3. The method of claim 1 wherein the step of characterizing a touch probe further comprises computing the touch probe radius based on the axis positions of the touch probe at a plurality of predetermined positions.

4. The method of claim 3 wherein the predetermined positions includes one or more of about zero degrees, about ninety degrees, about one hundred eighty degrees, and about two hundred seventy degrees.

5. The method of claim 1 wherein the step of characterizing a touch probe further comprises:
   guiding the touch probe over a surface of the component;
   creating a model of the component; and
   obtaining an inspection path from the model.

6. The method of claim 5 wherein the step of generating an inspection path further comprises:
   rotating the touch probe to a predetermined position;
   moving the touch probe toward the calibration plate; and
   recording an axis position of the touch probe.

7. The method of claim 6 further comprising repeating the steps of rotating the touch probe, moving the touch probe and recording an axis position until the touch probe is substantially calibrated.

8. The method of claim 6 wherein the predetermined position includes one or more of about zero degrees, about ninety degrees, about one hundred eighty degrees, and about two hundred seventy degrees.

9. The method of claim 1 wherein the step of aligning a component with the touch probe further comprises calibrating a true center of the component, the step of calibrating the true center of the component comprises contacting the touch probe to the component at a plurality of predetermined positions of the component and recording the location of the points.

10. The method of claim 9 wherein the plurality of predetermined positions of the component includes two or more of substantially the top-center of the component, substantially the top-right of the component, substantially the top-left of the component, substantially the bottom center of the component; substantially the bottom-left of the component or substantially the bottom-right of the component.

11. The method of claim 9 wherein the step of transferring the virtual zero point of the touch probe to a virtual zero point of the eddy current probe further includes using a software interface to transfer the recorded locations of the points from the touch probe to the eddy current probe.

12. The method of claim 9 wherein the step of transferring the virtual zero point of the touch probe to a virtual zero point of the eddy current probe further includes adjusting an offset value of the component based on the recorded locations of the points from the touch probe and the touch probe radius.

13. A method for eddy current inspection of a component comprising:
   providing a touch probe, the touch probe being an alignment tool;
   aligning an eddy current probe for eddy current inspection of the component using the touch probe;
   initializing a scan plan of the component;
   completing the eddy current inspection of the component; and
   wherein the aligning the eddy current probe for eddy current inspection of the component using the touch probe eliminates parameter adjustments during the eddy current inspection of the component.

14. The method of claim 13 wherein the step of aligning an eddy current probe for eddy current inspection of the component further comprises:
   characterizing the touch probe with a calibration plate to find a probe radius and a probe offset of the touch probe;
   aligning the component to be inspected with the touch probe to locate and place a virtual zero point of a model of the component to a virtual zero point of the component;
   transferring a virtual zero point of the touch probe to a virtual zero point of the eddy current probe; and
   wherein the probe radius and the probe offset are entered into coordinates that are transferred to the eddy current probe to compensate for any abnormalities or imperfections in the touch probe during the step of aligning the component with the touch probe.

15. The method of claim 14 wherein the step of characterizing a touch probe further comprises computing the touch probe offset based on the probe radius.

16. The method of claim 14 wherein the step of characterizing a calibration plate further comprises computing the touch probe radius based on the axis positions of the touch probe at a plurality of predetermined positions.

17. The method of claim 16 wherein the predetermined positions includes one or more of about zero degrees, about ninety degrees, about one hundred eighty degrees, and about two hundred seventy degrees.

18. The method of claim 14 wherein the step of aligning a component with the touch probe further comprises calibrating a true center of the component, the step of calibrating the true center of the component comprises contacting the touch probe to the component at a plurality of predetermined positions of the component and recording the location of the points.

19. The method of claim 18 wherein the plurality of predetermined position of the component includes two or more of substantially the top-center of the component, substantially the top-right of the component, substantially the top-left of the component, substantially the bottom center of the component; substantially the bottom-left of the component or substantially the bottom-right of the component.

20. The method of claim 14 wherein the step of transferring the virtual zero point of the touch probe to a virtual zero point of the eddy current probe further includes using a software interface to transfer the recorded locations of the points from the touch probe to the eddy current probe.

21. The method of claim 20 wherein the step of transferring the virtual zero point of the touch probe to a virtual zero point of the eddy current probe further includes adjusting an offset value of the component based on the recorded locations of the points from the touch probe and the touch probe radius.

22. The method of claim 14 wherein the step of characterizing a touch probe further comprises:
   guiding the touch probe over a surface of the component;
   creating a model of the component; and
   obtaining an inspection path from the model.

23. The method of claim 22 wherein the step of generating an inspection path further comprises:
   rotating the touch probe to a predetermined position;
   moving the touch probe toward the calibration plate; and
   recording an axis position of the touch probe.

24. The method of claim 22 further comprising repeating the steps of rotating the touch probe, moving the touch probe and recording an axis position until the touch probe is substantially calibrated.

25. The method of claim 15 wherein the predetermined position includes one or more of about zero degrees, about ninety degrees, about one hundred eighty degrees, and about two hundred seventy degrees.

* * * * *